(12) United States Patent
Dick et al.

(10) Patent No.: US 8,728,062 B2
(45) Date of Patent: May 20, 2014

(54) DEVICE AND METHOD FOR CONTROLLING A LASER THERAPY OF THE EYE

(75) Inventors: Manfred Dick, Gefell (DE); Martin Hacker, Jena (DE); Michael Kempe, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 294 days.

(21) Appl. No.: 13/070,217

(22) Filed: Mar. 23, 2011

(65) Prior Publication Data

US 2011/0238046 A1   Sep. 29, 2011

(30) Foreign Application Priority Data

Mar. 23, 2010   (DE) .................... 10 2010 012 810

(51) Int. Cl.
*A61B 18/20* (2006.01)
*A61B 3/10* (2006.01)
*A61B 5/15* (2006.01)
*A61B 5/00* (2006.01)

(52) U.S. Cl.
CPC . *A61B 3/102* (2013.01); *A61B 5/15* (2013.01); *A61B 5/0093* (2013.01)
USPC .......................................................... 606/5

(58) Field of Classification Search
CPC ............... A61B 5/0075; A61B 5/0066; A61B 2019/5231; A61B 5/015; A61B 5/0093; A61B 3/102; A61F 2009/00844; A61F 2009/00872
See application file for complete search history.

(56) References Cited

U.S. PATENT DOCUMENTS

| 4,741,612 | A | 5/1988 | Birngruber et al. |
| 6,006,756 | A | 12/1999 | Shadduck |
| 6,099,521 | A | 8/2000 | Shadduck |
| 7,357,570 | B2 | 4/2008 | Schuele |
| 2003/0032949 | A1 | 2/2003 | Schuele et al. |
| 2008/0177256 | A1* | 7/2008 | Loesel et al. ...................... 606/4 |
| 2010/0145319 | A1 | 6/2010 | Zimare et al. |
| 2011/0170111 | A1* | 7/2011 | Rolland et al. ................. 356/479 |
| 2013/0023865 | A1* | 1/2013 | Steinke et al. ..................... 606/7 |

FOREIGN PATENT DOCUMENTS

| DE | 30 24 169 A1 | 1/1982 |
| DE | 39 36 716 A1 | 5/1991 |
| DE | 101 35 944 A1 | 2/2003 |
| DE | 103 01 416 B3 | 7/2004 |
| DE | 10 2007 005 699 A1 | 8/2008 |

OTHER PUBLICATIONS

Dubois, Arnaud, et al., "Ultrahigh-resolution full-field optical coherence tomography," *Applied Optics*, vol. 43, No. 14 (May 10, 2004), pp. 2874-2883.

(Continued)

*Primary Examiner* — Gary Jackson
*Assistant Examiner* — Scott T Luan
(74) *Attorney, Agent, or Firm* — Patterson Thuente Pedersen, P.A.

(57) ABSTRACT

A device for controlling a laser therapy of the eye, including an evaluation unit that determines an intensity of a transient temperature effect by analysis of interferometric signals obtained from the eye and a control unit that controls the laser therapy, which is based on said transient temperature effect, the control unit being connected with said evaluation unit. A method for controlling a laser therapy of the eye, includes determination of the intensity of a transient temperature effect that is utilized for the control of the laser therapy, based on the effect, by analysis of interferometric signals.

5 Claims, 2 Drawing Sheets

(56) References Cited

OTHER PUBLICATIONS

Park, B. Hyle, et al., "In vivo burn depth determination by high-speed fiber-based polarization sensitive optical coherence tomography," *Journal of Biomedical Optics*, vol. 6, No. 4 (Oct. 2001), pp. 474-479.

Laubscher, Markus, et al., "Video-rate three-dimensional optical coherence tomography," *Optics Express*, vol. 10, No. 9 (May 6, 2002), pp. 429-435.

Yazdanfar, Siavash, et al., "Frequency estimation precision in Doppler optical coherence tomography using the Cramer—Rao lower bound," *Optics Express*, vol. 13, No. 2 (Jan. 24, 2005), pp. 410-416.

Zhao, Yonghua, et al., "Doppler standard deviation imaging for clinic monitoring of in vivo human skin blood flow," *Optics Letters*, vol. 25, No. 18 (Sep. 15, 2000), pp. 1358-1360.

Leitgeb, R., et al., "Spectral measurement of absorption by spectroscopic frequency—domain optical coherence tomography," *Optics Letters*, vol. 25, No. 11 (Jun. 1, 2000), pp. 820-822.

Choma, Michael A., et al., "Spectral—domain phase microscopy," *Optics Letters*, vol. 30, No. 10 (May 15, 2005), pp. 1162-1164.

Serov, Alexandre, et al., "Full-field laser Doppler perfusion imaging and Monitoring with an intelligent CMOS camera," *Optics Express*, vol. 13, No. 10 (May 16, 2005), pp. 3681-3689.

\* cited by examiner

DEVICE AND METHOD FOR CONTROLLING A LASER THERAPY OF THE EYE

CLAIM TO PRIORITY

This application claims priority to German Patent Application No. 10 2010 012 810.4, filed on Mar. 23, 2010, said application is incorporated herein by reference in its entirety.

FIELD OF THE INVENTION

The invention relates to a device and a method for controlling laser therapy of the eye.

BACKGROUND

DE 30 24 169 describes a method for operating a photocoagulator for biological tissue.

DE 39 36 716 describes a device for the thermal changes of biological tissue.

However, the devices described in both publications are disadvantageous in that tissue worthy of preservation is destroyed during their application (particularly, the photoreceptor layer located in beam direction in front of the retinal pigment epithelium). Therefore, the task of providing a coagulation system for the coagulation of organic tissues that minimizes the destruction of tissue worthy of preservation has already been considered in the past, whereby the local treatment is terminated once a defined temperature is reached at the coagulation point.

DE 101 359 44 is an example thereto. Therein, a temperature-controlled coagulation system for the coagulation of organic tissues, particularly the retina, is described which comprises a continuous coagulation laser and a pulsed measuring laser, a detector, a control device, and an interrupter, whereby the coagulation laser is designed to emit a coagulation beam and the measuring laser is designed to generate in the target area of the coagulation laser a temperature-dependent measurement signal for the detector; whereby the detector exhibits a temperature sensor, which evaluates the effect of the applied radiation, and which is designed to detect a signal and to transmit the detection of a signal to the control device; wherein the control device is designed to activate an interrupter; whereby the interrupter is designed to interrupt the emission of waves with a wavelength at least that of the working beam of the laser; and whereby the signal corresponds to a degree of coagulation and/or the temperature of the tissue.

Said solution for a temperature-controlled laser photocoagulation is disadvantageous because only one temperature measuring system capable of controlling the integral temperature profile within a coagulation spot during a laser coagulation can be provided, and measurement signals are only obtained when there is contact with the eye.

In DE 103 01 416 B1, the entire content of which is incorporated by reference, a device and a method for non-contact temperature control and adjustment is described, by a temperature change is to be determined interferometrically at the coagulation spot. Thereby, said document proceeds on the assumption that through the temperature change a refractive index change occurs in a defined volume which is subsequently determined interferometrically. However, as already described therein, such effect is very low since the temperature-induced change of the refractive index and the expansion of the measurement volume partially cancel each other out. OCT (optical coherence tomography) is also mentioned in said document as a method of analysis.

SUMMARY OF THE INVENTION

It is the task of the invention to overcome the disadvantages of prior art and to define a more precise option for controlling a therapy laser for the coagulation of tissue at the eye fundus.

Thereto, the solution, according to the invention, provides a device for optical coherence tomography (OCT) which can produce a three-dimensional image of tissue structures due to the scattering and/or reflection properties of the tissue. Thereby, the various technological embodiments of an OCT-system can be applicable. Those are systems that are based on the time domain and particularly on the spectral domain principle. Thereby, said systems perform an A-scan in the direction of the optical irradiation direction in the tissue in order to obtain the depth information from the particularly hydrous tissue. Furthermore, a so-called B-scan can be performed through the lateral deflection of the measurement beam in order to obtain sectional images of the tissue.

A three-dimensional volume can thus be depicted from several B-scans. The wavelengths of the OCT-system are selected in the transparent and/or partially transparent range of the tissue to be examined, particularly in the near infrared range of approximately 700-1400 nm.

Furthermore, the solution, according to the invention, provides a therapeutically acting laser system, the particularly pulsed radiation of which is irradiated onto the tissue to be treated, particularly the retina.

Therefore, the solution, according to the invention, includes the combination of the therapy of the eye tissue and a simultaneous, particularly synchronized examination of exactly the same tissue with a fast OCT-system. Thereby, the signaling of the OCT-system is based on the scattering and/or reflection of the tissue components which are usually arranged within time ranges smaller than 10 ms at relative rest to the OCT-system. Through the thermal excitation of the target area in the tissue examined by the OCT, the scattering/reflecting tissue particles are, due to their absorption properties, also moved and, accordingly, induce on the A-scan OCT signal an additional Doppler frequency and/or beat frequency, which can be analyzed. The radiation of the optoacoustic laser, absorbed at the fundus of the eye, particularly in the RPE, leads to instantaneous warming. Said warming leads to an increase in pressure since the density of the tissue decreases during warming. The increase of the pressure within the absorber (e.g., RPE) rises and scales with the dimensionless, temperature-dependent Grueneisen coefficient. As a result, a connection of the Brownian motion of the absorbing particles, which simultaneously appear as scattering/reflecting particles in the OCT image, and the temperature is established, which, according to the invention, is determined via the analysis of the A-scan OCT signal and spatially assigned to the tissue structure.

Alternatively to a detection of the signal via an A-scan, the change of the spectrum of the scattered light, which is connected to the temperature change (through the movement of scattering centers in the tissue), can also be analyzed parallel in the entire image field.

Thereto, either the reflected light is superimposed with light from a reference arm, or the speckle pattern, caused by the reflected and scattered light, is detected and analyzed. In the first case, this corresponds to an arrangement which is known as full-field OCT, e.g., from Dubois et al., APPLIED OPTICS Vol. 43, No. 14 May 2004, pp. 2874-2883. However, in order to achieve the required high sampling rate in the microsecond range, the use of an intelligent CMOS camera (see, e.g., Laubscher et al., Optics Express, Vol. 10 Issue 9, pp. 429-435 (2002)) is advantageous. Through the use of short-coherent light (e.g., a conventional white light source), the Doppler signal can be obtained depth selectively, e.g., directly from the RPE. In the case of the detection of a speckle pattern, caused through scattering of a temporally coherent light source (e.g., a narrow-band laser) on the tissue, an integral signal about the depth of the retina is obtained. The arrangement and the measuring principle is similar to the prior art described in Serov et al., OPTICS EXPRESS Vol. 13, No. 10 May 2005, pp. 3681-3689. Parallel methods are particularly advantageous when the warming of the tissue is performed in a larger area or simultaneously at several points on the retina.

Therefore, the invention comprises a device for controlling a laser therapy of the eye, wherein means are provided for the determination of the intensity of a transient temperature effect by means of the analysis of interferometric signals, and that means for the control of the laser therapy, which is based on said effect, are connected with said former means.

Thereby, said interferometric signals can be OCT signals, wherein the analysis is particularly a method from the group polarization analysis (PSOCT), phase analysis (SPDM), Doppler analysis (DOCT), spectroscopic analysis (spectrally resolved OCT), or speckle distribution analysis.

Furthermore, according to the invention, means for the control of the laser therapy are configured in such a way that tissue with defined OCT characteristics is automatically included in or excluded from the laser therapy.

The method for controlling a laser therapy of the eye, according to the invention, is characterized in that the determination of the intensity of a transient temperature effect is utilized for the control of the laser therapy, based on said effect, by means of the analysis of interferometric signals.

Thereby, it is advantageous for the interferometric signals to be OCT signals, wherein the analysis is particularly a method from the group polarization analysis (polarization-sensitive OCT—PSOCT), phase analysis (spectral-domain phase microscopy—SPDM), Doppler analysis (Doppler OCT—DOCT), spectroscopic analysis (spectrally resolved OCT), or speckle distribution analysis.

The method is particularly advantageous when the tissue with defined OCT characteristics is automatically included in or excluded from the laser therapy. Furthermore, the invention comprises a method for the realization of a three-dimensional, preferably time-resolved ophthalmological thermography, wherein a Doppler broadening distribution $\Omega(x,y,z,t)$ is determined by means of a Doppler OCT (DOCT), and a temperature distribution is determined therefrom.

Said temperature distribution is determined in accordance with $$T(x, y, z, t) = \alpha \frac{\Omega(x, y, z, t) \cdot 3\eta a \lambda_0^2}{16\pi k_b}$$

wherein $\Omega$ is the Doppler frequency spread determined by DOCT; wherein $k_b$ is the Boltzmann constant; wherein $\eta$ is the dynamic viscosity of the medium; wherein $a$ is the particle diameter; wherein $\lambda_0$ is the OCT spectral centroid; and wherein $\alpha$ is a material characteristic.

Then, said temperature distribution T can be utilized advantageously for the control of the laser therapy, particularly also because the temperature profile and therefore an introduced energy dose can be determined with said method.

When utilizing the method of polarization analysis (PSOCT), the transient temperature effect can be a temperature-dependent loss of the polarizing effect in nerve fiber tissues.

In the phase analysis (SPDM), the transient temperature effect can be a material expansion (tissue expansion).

In the Doppler analysis (Doppler OCT, DOCT), the transient temperature effect can be a change of the Doppler bandwidth.

In the spectroscopic analysis (spectrally resolved OCT), the transient temperature effect can be a change of tissue absorptions or tissue fluorescences.

In the speckle distribution analysis, the transient temperature effect can be a change of the velocity distributions of Brownian motions of particles or alternatively also the change of the speckle distribution in the retina reflection of a long-coherent (i.e., a coherence length >1 mm) light source due to a change of the retinal surface. In the Doppler analysis (Doppler OCT, DOCT), the transient temperature effect can also be a change of the expansion or contraction velocities or directions of tissue components or alternatively also a change of the blood flow in vessels.

The underlying physical correlations of the aforementioned methods are, among others, described in the following citations, the contents of which are hereby incorporated by reference:

DOCT: The analysis of phase information in OCT signals for the isolation of Doppler signals for the determination of movements (DOCT), particularly of blood flows ("Doppler Standard Deviation Imaging for Clinical Monitoring of In Vivo Human Skin Blood Flow" Y. Zhao, Z. Chen, C. Saxer, Q. Shen, S. Xiang, J. F. de Boer, J. S. Nelson, Opt. Lett. 25, 1358 (2000)).

PSOCT: The determination of the Doppler diffraction loss in collagens of the skin due to burns by means of polarization-sensitive OCT (PSOCT, B. H. Park, C. Saxer, S. M. Srinivas, J. S. Nelson, J. F. de Boer, J. Biomed. Opt. 6 (4), 474 (2001)).

SPDM: The determination of temperature-induced thickness changes of glass plates by means of spectral domain phase microscopy (SDPM, M. A. Choma, A. K. Ellerbee, C. H. Yang, T. L. Creazzo, J. A. Izatt, Opt. Lett. 30 (10), 1162 (2005)).

SOCT: Analysis of signals of the spectroscopic OCT (SOCT, R. Leitgeb, M. Wojtkowski, A. Kowalczky, C. K. Hitzenberger, M. Sticker, A. F. Fercher, Opt. Lett. 25, 820 (2000)).

It is further known that Doppler analyses are disturbed by temperature effects (Frequency estimation precision in Doppler optical coherence tomography using the Cramer-Rao lower bound. Siavash Yazdanfar, Changhuei Yang, Marinko V. Sarunic, Joseph A. Izatt, 24 Jan. 2005/Vol. 13, No. 2/OPTICS EXPRESS 410).

DETAILED DESCRIPTION

Figure 1:
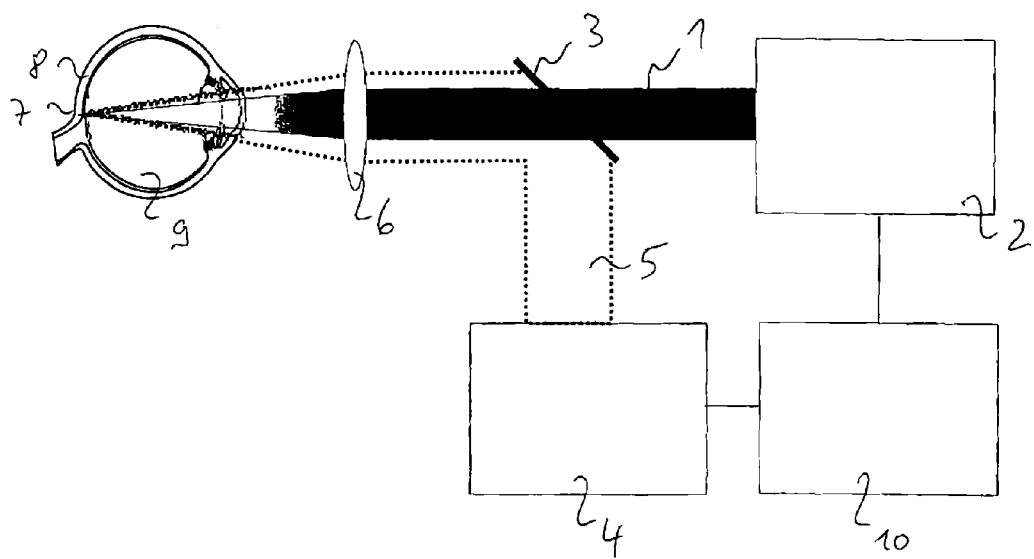
FIG. 1 is a schematic depiction of a device according to an embodiment of the invention.

The device schematically depicted in FIG. 1 includes a measurement beam 1 producing beam source/analyzer 2 (e.g., an OCT system), a dichroic mirror 3, which combines the therapy beam 5 produced by a therapy beam source 4 with the measurement beam 1 and which focuses via imaging optics 6 on the target area 7 of a retina 8 of the eye 9.

The therapy beam source 4 emits light pulses of, e.g., 1 ps with a wavelength of, e.g., 532 nm, which, upon impinging on the retina, trigger an optoacoustic pulse which is optically detected by the analyzer 2 and evaluated by the evaluation unit 10, e.g., by means of the analysis of an OCT image. As already described, the temperature of the tissue can be extrapolated from said analysis, and such information is then used for the control of the therapy beam source 4.

Figure 2:
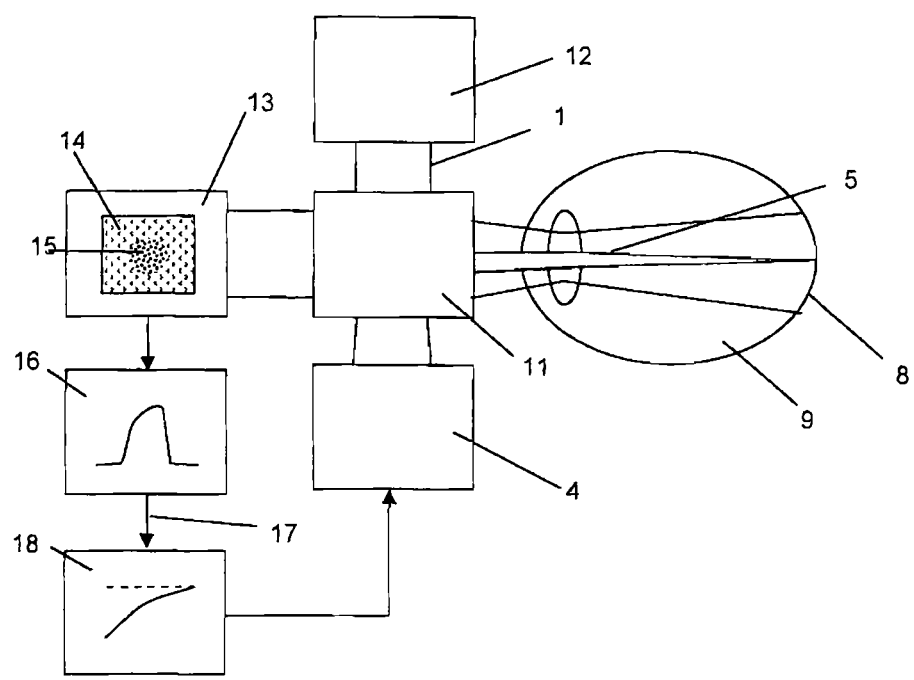
FIG. 2 is a schematic depiction of a device according to an embodiment of the invention.

FIG. 2 also schematically depicts an embodiment of the invention, wherein the speckle distribution is determined as transient temperature effect. Via optics 11 for combining the therapy beam 5 from the therapy laser 4 with the measurement beam 1 of the measurement beam source 12, the combined beam is focused on the retina 8 of the eye 9. The spatially resolving detector 13 for the acquisition of the retina image 14 with the exemplarily indicated change of the speckle structure 15 is connected to an evaluation unit 16 which produces a temperature effect signal 17 (e.g., through high-pass filtering and summation) from said change.

Said signal 17 is passed on to a control unit 18 which controls the therapy laser 4 in dependency of the integrated temperature effect signal 17, particularly through deactivation once a predetermined (effect) dose is reached.

The measuring laser 12 must exhibit a sufficient coherence length for the generation of speckles, i.e., greater than 1 mm, and the wavelength is preferably in the infrared range, i.e., 700-1300 nm. The detector 13 must exhibit a sufficient spatial resolution for the speckles and a temporal resolution of 5 µs to 100 ms, preferably 100 µs, in order to temporally detect with sufficiency the transient effects of the change of the speckles due to the effect of the therapy beam on the tissue.

The invention claimed is:

1. A device for controlling laser therapy of an eye, comprising:
    an evaluation unit that determines an intensity of a transient temperature effect in the eye by analysis of interferometric signals obtained from the eye; and
    a control unit that controls a laser that applies the laser therapy, which is based on said transient temperature effect, the control unit being operably connected with said evaluation unit;
    an OCT and wherein said interferometric signals are OCT signals, and further wherein the analysis comprises Doppler analysis (DOCT);
    wherein the evaluation unit is configured to determine a temperature distribution according to the following relationship:

$$T(x, y, z, t) = \alpha \frac{\Omega(x, y, z, t) \cdot 3\eta a \lambda_0^2}{16\pi k_b}$$

wherein $\Omega$ is the Doppler frequency spread determined by DOCT; wherein $k_b$ is the Boltzmann constant; wherein $\eta$ is a dynamic viscosity of a medium; wherein a is a particle diameter; wherein $\lambda_0$ is an OCT spectral centroid; and wherein $\alpha$ is a material characteristic.

2. The device, according to claim 1, wherein the control unit that controls the laser therapy is configured such that tissue with defined OCT characteristics is automatically included in or excluded from the laser therapy.

3. A computer implemented method of creating a three-dimensional, ophthalmological thermography, comprising:
    determining a Doppler broadening distribution $\Omega(x,y,z,t)$ by use of a Doppler OCT (DOCT); and
    determining a temperature distribution from the Doppler broadening distribution to create the thermography by use of a computer controller;
determining the temperature distribution according to the following relationship:

$$T(x, y, z, t) = \alpha \frac{\Omega(x, y, z, t) \cdot 3\eta a \lambda_0^2}{16\pi k_b}$$

wherein $\Omega$ is the Doppler frequency spread determined by DOCT; wherein $k_b$ is the Boltzmann constant; wherein $\eta$ is a dynamic viscosity of a medium; wherein a is a particle diameter; wherein $\lambda_0$ is an OCT spectral centroid; and wherein $\alpha$ is a material characteristic.

4. The method, according to claim 3, further comprising determining the ophthalmological thermography on a time resolved basis.

5. A computer implemented method of controlling a laser therapy of the eye, comprising:
    using a temperature distribution T to control a laser applying the laser therapy; and
    determining the temperature distribution T using the following relationship $$T(x, y, z, t) = \alpha \frac{\Omega(x, y, z, t) \cdot 3\eta a \lambda_0^2}{16\pi k_b}$$

wherein $\Omega$ is the Doppler frequency spread determined by DOCT; wherein $k_b$ is the Boltzmann constant; wherein $\eta$ is a dynamic viscosity of a medium; wherein a is a particle diameter; wherein $\lambda_0$ is an OCT spectral centroid; and wherein $\alpha$ is a material characteristic.

* * * * *